(12) United States Patent
Cosman

(10) Patent No.: US 6,167,710 B1
(45) Date of Patent: Jan. 2, 2001

(54) ICE SEEDING APPARATUS FOR CRYOPRESERVATION SYSTEMS

(75) Inventor: Maury D. Cosman, Woburn, MA (US)

(73) Assignee: Organogenesis Inc., Canton, MA (US)

( * ) Notice: Under 35 U.S.C. 154(b), the term of this patent shall be extended for 0 days.

(21) Appl. No.: 09/117,412

(22) PCT Filed: Jan. 30, 1997

(86) PCT No.: PCT/US97/01619

§ 371 Date: Dec. 17, 1998

§ 102(e) Date: Dec. 17, 1998

(87) PCT Pub. No.: WO97/28402

PCT Pub. Date: Aug. 7, 1997

Related U.S. Application Data

(63) Continuation-in-part of application No. 08/593,587, filed on Jan. 30, 1996, now Pat. No. 5,689,961.

(51) Int. Cl.$^7$ ........................................ F24F 3/16
(52) U.S. Cl. .................................. 62/78; 62/373
(58) Field of Search ................... 62/78, 64, 51.1, 62/237, 373; 211/188, 194, 211

(56) References Cited

U.S. PATENT DOCUMENTS

| | | | |
|---|---|---|---|
| 3,905,206 * | 9/1975 | Deubel et al. | 62/373 |
| 4,107,937 * | 8/1978 | Chmiel | 62/64 |
| 4,739,625 * | 4/1988 | Buchmuller et al. | 62/209 |
| 5,309,722 * | 5/1994 | Philips, Jr. | 62/49.1 |
| 5,475,983 * | 12/1995 | Yamamoto et al. | 62/62 |
| 5,813,537 * | 9/1998 | Grace et al. | 62/52.1 |

* cited by examiner

Primary Examiner—Pamela Wilson
(74) Attorney, Agent, or Firm—Hale and Dorr LLP

(57) ABSTRACT

An apparatus for ice seeding during cryopreservation of biological samples such as cells, harvested tissues, and cellular biological constructs such as culture tissues equivalents wherein ice seeding is performed by discharging a liquefied or chilled gas from a nozzle to the surface container containing the biological sample in cryopreservative. Inside a freezing chamber, containers are placed on racks that are located proximal to a sprayrail containing nozzles. Ice seeding is performed by discharge of liquefied or chilled gas from the nozzles to the container surface at the solid-liquid equilibrium temperature of the cryopreservative. Localized cooling of the container surface by the discharge results in ice seed formation within the container.

17 Claims, 7 Drawing Sheets

ICE SEEDING APPARATUS FOR CRYOPRESERVATION SYSTEMS

CROSS-REFERENCED TO RELATED APPLICATIONS

This application claims priority under 35 U.S.C. § 371 from PCT/US97/01619 filed Jan. 30, 1997, and is a continuation-in-part of application Ser. No. 08/593,587, filed Jan. 30, 1996, now U.S. Pat. No. 5,689,961.

BACKGROUND OF THE INVENTION

1. Field of the Invention

This invention relates to an ice seeding apparatus for cryopreservation systems for biological samples such as cells, harvested tissue and cellular biological constructs such as cultured tissue equivalents. Ice seeding in a cryopreservation protocol initiates the formation of ice that is controllable to allow for maximal viability of the tissue or tissue equivalent to be cryopreserved after it has been subsequently thawed. By use of the cryopreservation technology, either cryopreserved harvested tissue or cryopreserved cultured tissue may be stored for indefinite periods of time prior to use. The cultured tissue is an in vitro model of the equivalent human tissue, which, when retrieved from storage, can be used for transplantation or implantation, in vivo, or for screening compounds in vitro.

2. Brief Description of the Background of the Invention

Heretofore, the cryopreservation of cadaver tissue and cultured tissue equivalents for the purposes of preserving the viability of the cells in the tissue has been achieved, but with limited success. Currently, the storage time of cellular biological materials is extended by cooling to "cryogenic" temperatures.

The transition from the liquid into the solid state by lowering the temperature of the system can take place either as crystallization (ice), involving an orderly arrangement of water molecules, or as vitrification or amorphization (glass formation), in the absence of such an orderly arrangement of crystalline phase. The challenge for a cryobiologist is to bring cells to cryogenic temperatures and then return them to physiological conditions without injuring them.

There are two basic approaches to cryopreservation of cells and tissues: freeze-thaw and vitrification. In freeze-thaw techniques, the extracellular solution is frozen (i.e., in crystalline form), but steps are taken to minimize the intracellular ice formation. In vitrification procedures, there is an attempt to prevent crystalline ice formation throughout the cells and tissue. The former approach is problematic in that if ice crystals are formed inside the cells, they are detrimental to cell viability upon thawing. However, cells could survive a freeze-thaw cycle if they are cooled at controlled rates in the presence of non-toxic levels of cryoprotectants. The latter approach of vitrification seeks to avoid potentially damaging affects of intra- and extracellular ice by depressing ice formation by the addition of very high concentrations of solutes and/or polymers. However, cell damage may occur from long exposure to toxic levels of these additives required for vitrification.

Cryoprotectants protect living cells from the stresses involved in the freezing process. One way cryoprotectants protect cells is by diluting the salt that becomes increasingly concentrated in the unfrozen solution as water is transformed to ice. The amount of ice is dictated by the temperature and initial composition of the solution; whereas the amount of unfrozen fraction is a function of temperature only. Cryoprotectants have several other functions. An important one is that they usually reduce the intracellular ice formation during freezing and thawing of a biological sample. Another function is that they stabilize membranes and proteins. Once the extracellular ice is seeded and the sample is surrounded by the ice phase, it is necessary to cool the sample to a cryopreserved state. The cooling step is one of the most critical steps in a freeze-thaw protocol. Due to the formation of ice, that is, pure water, the partially frozen extracellular solution is more concentrated than the intracellular compartment. As a consequence, the cell will dehydrate by losing water in an attempt to restore thermodynamic equilibrium. As the system cools, more extracellular ice is generated and the concentration of solutes rises and forces the cells to dehydrate further. There are three characteristics of the cells that control their rate of dehydration. One is the cell membrane water permeability; the lower the water permeability, the longer it takes for the cells to dehydrate. Another is the temperature dependence of the cell membrane water permeability; water permeability decreases with decreasing temperatures. The final is cell size; larger cells take longer to dehydrate than smaller cells. Given that each cell type may have drastically different characteristics, the optimal cryopreservation conditions can vary by orders of magnitude for different cell types.

All solutions will supercool below their freezing point until they find a random nucleation site for crystal formation. When cryopreserving by a freeze-thaw method, ice formation in the extracellular medium should be deliberately initiated by seeding at low degrees of supercooling. If ice formation is not induced by seeding, ice will form spontaneously when the solution is cooled sufficiently far below its equilibrium freezing point. Because this process is random in nature, ice formation will occur at random, unpredictable temperatures. Consequently, survival rates will be highly variable between repeated trials with the same freezing protocol. Furthermore, the extremely rapid crystallization which results when ice forms in a highly supercooled solution can cause damage to cells and tissues. Moreover, it has been shown that if extracellular ice formation is initiated at high degrees of supercooling, the probability of intracellular ice formation is drastically increased. This phenomenon results from the delayed onset of freeze-induced cell dehydration, which results in increased retention of intracellular water, and thus higher likelihood of ice formation in the cell.

Although the exact mechanisms of cell damage during cryopreservation have not yet been completely elucidated, cell survival as a function of cooling rate appear to be qualitatively similar for all cell types and displays an inverted U-shaped curve. Cell survival is low at very slow and very fast cooling rates, and there is an intermediate cooling rate yielding optimal survival. Even though the optimal cooling rate and the width of the curve can vary drastically for different cell types, the qualitative behavior appears to be universal. Faster cooling rates do not allow cells enough time to dehydrate and cells therefore form ice internally. Cell injury at fast cooling rates is attributed to intracellular ice formation. At slow rates of cooling, cell injury is thought to be due to the effects of exposure to highly concentrated intra- and extracellular salt and cryoprotectant solutions or to the mechanical interactions between cells and the extracellular ice.

It is necessary to dehydrate the cells as much as possible before they cross 30 the intracellular ice nucleation curve. It is at this point that water remaining in the cell will nucleate and form ice. The temperature where this will happen is approximately −40° C. to −50° C. when the cells are slowly frozen in the presence of 1M to 2M concentrations of cryoprotectants. It is important to note that the amount of water that turns to ice inside a cell at this point may be innocuous when frozen, but if not thawed fast enough, rearrangement of ice may kill the cell upon thawing. (*The Biophysics of Organ Cryopreservation*, Pg. 117–140, edited by David E. Pegg and Armand M. Karow, Jr. NATO ASI Series A: Life Sciences Vol. 147 1987 Plenum Press, New York 233 Spring St., New York, N.Y. 10013).

Other cryopreservation systems, particularly those relating to the freezing of biological samples comprising cells either seed ice by another means, as in chamber spike methods or by use of electronic or mechanical means, or do not seed ice at all.

To seed ice using chamber spike methods, a chamber containing biological samples, such as vials of cells, is quickly cooled to a temperature well below the freezing (i.e., liquid-solid equilibrium temperature) point of the cryopreservation medium then the temperature is raised quickly to near the equilibrium temperature. A drawback to this method is that chamber temperature variations create problems for uniform ice seeding. In many cases, overseeding of ice in the samples occurs resulting in cell damage.

Electronic methods use thermoelectric elements based on semiconductor thermocouples that can controllably produce local cooling. Interfacing these thermoelectric elements with the surface of a container or package containing a biological sample is difficult and variations in effective cooling of the container surface can occur.

Mechanical means of providing localized cooling by use of cold probes, bars or pins to contact the side of a container is problematic in that the process is labor intensive and requires opening the thermal chamber or development of sophisticated mechanisms for guiding the cold probe.

Accordingly, it has long been desired to provide a better method of cryopreserving harvested tissue and cultured tissue equivalents to improve cell viability after the tissue has subsequently been thawed. The inventors of the present invention have developed a novel apparatus and method of inducing ice formation in cryopreservation solution, contained in a package with tissue to be frozen, that allows for consistent and reliable seeding of ice of a sufficient amount. The apparatus is standardized and is expandable with additional fixtures added to the apparatus.

SUMMARY OF THE INVENTION

The apparatus and method of the present invention provide for cryopreservation of biological specimens such as cells, tissues and tissue equivalents, and maintains their viability after subsequent thawing. Cryopreservation is performed in a freezing chamber at a controlled freezing rate. Tissues and tissue equivalents are perfused with a cryoprotective medium while agitated. Specimens are sealed in a package containing cryoprotective medium and cooled to or slightly below the liquid-solid equilibrium temperature of the medium. At that temperature, the ice seeding is performed, resulting in a seed of ice in the medium. The temperature is held constant for a sufficient amount of time to allow equilibration between the liquid and solid phases. The temperature of the chamber is then lowered at a slow rate to an intermediate temperature; then rapidly to a cryogenic temperature.

In the preferred embodiment, ice seeding is accomplished by discharging a liquefied or chilled gas, preferably freon, from the sprayrails to adjacent racks containing tissue equivalent samples packaged in cryoprotectant. The freon discharged contacts the exterior surface of the package and evaporates. The heat transfer from the package due to the evaporation of the freon results in local cooling in the cryoprotective medium at the freon contact site within the package. Sufficient cooling of the medium at that site causes a degree of ice formation, an ice seed, in the medium. The apparatus for cooling preferably has a vertically-oriented sprayrail with nozzles at a position to be close to containers when mounted on a removable rack. The system can have multiple sprayrails and valves for directing the fluid to the desired sprayrail.

An advantage of the ice seeding system is the ability to consistently form a seed of ice in a plurality of sealed packages containing cryoprotective medium and tissue or equivalents thereof. The cryopreservation apparatus and method of the present invention can be used in the manufacturing process for storing and shipping of these tissues while frozen. The tissues are rendered viable when thawed.

The use of the ice seeding system in the cryopreservation process has demonstrated an application in the manufacturing process of living tissue equivalents. Prior to this invention, harvested tissue and living tissue equivalents had limited shelf-life and, subsequently, their window of use is short, resulting in much waste. There is a need to preserve such tissues for extended periods of time, as in shipping and storage, until their use. Previous attempts to freeze or freeze dry these tissues have been met with limited success and have compromised their use for grafting, in vivo, or for in vitro testing. The ability to use these tissues in a viable state represents an exceptional advantage of the present invention.

DETAILED DESCRIPTION OF THE INVENTION

Figure 1:
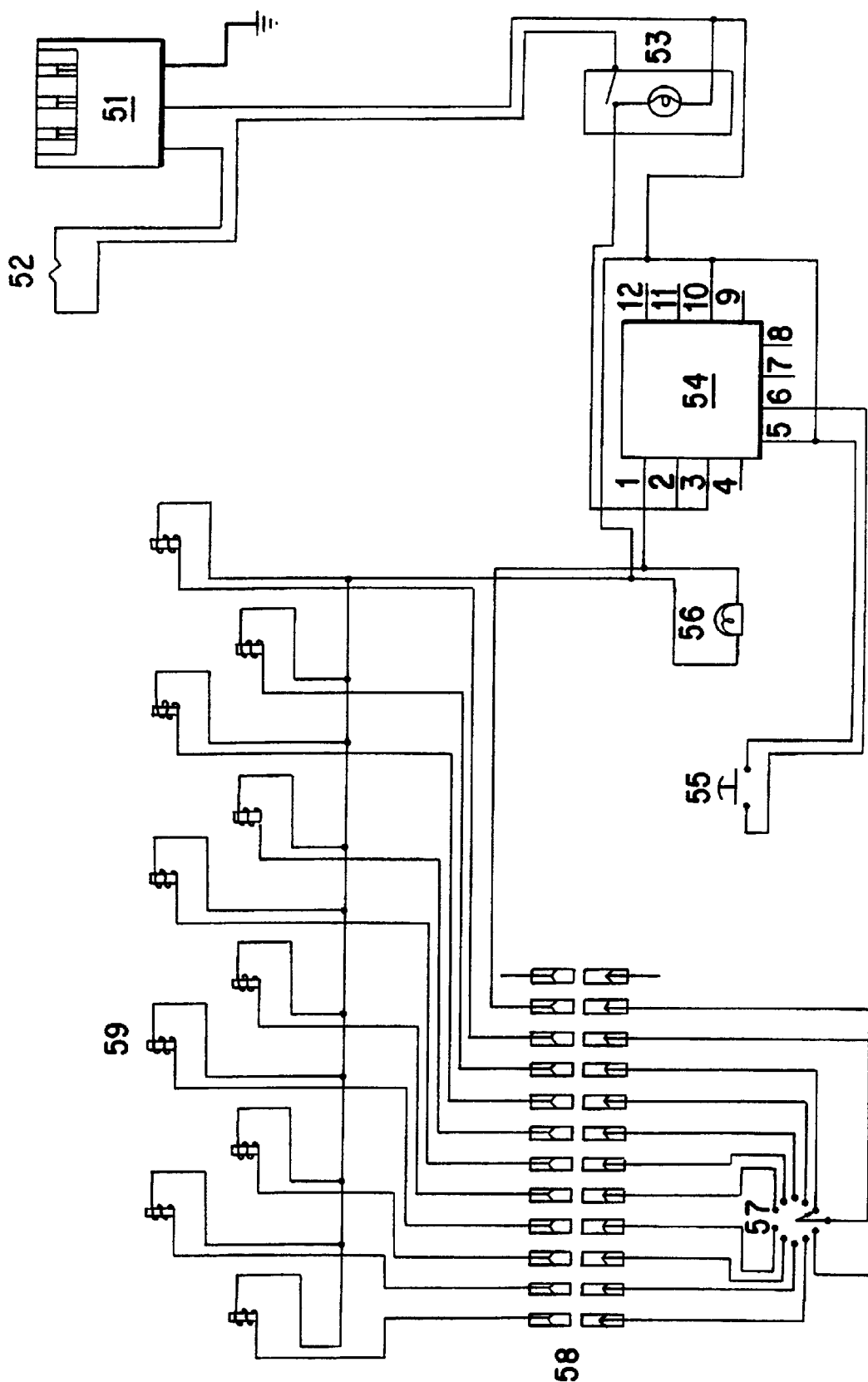
FIG. 1 depicts a electronic schematic of the ice seeding controller.

The purpose of the ice seeding system of the present invention is to initiate the formation of ice seeds in packages containing biological samples such as cells, tissue or tissue equivalents in a cryoprotective medium to be cryopreserved. Ice seeding must be accomplished within a temperature range slightly below the equilibrium freezing point of the cryoprotectant solution used. Ice seeds initiated above the freezing point may melt before cooling proceeds below this point. To preserve cell viability, ice seeding must be initiated in the cryopreservation medium outside of the tissue or cells. The invention performs ice seeding without causing ice to form within the tissue: A plug of ice is formed primarily in the cryoprotectant bordering the outside of the tissue.

The ice seeding apparatus comprises three major elements: A controller, spray rails, and racks. The ice seeding controller is a mechanism that regulates the flow of liquefied or chilled gas from a pressurized source to the chamber containing the items to be frozen for storage. By using a number of switches, ports, valves, a rack selector, and a timing mechanism, the controller centrally manages the operations of the system.

Regulation of liquefied or chilled gas discharge, herein also referred to as 'discharge', from a pressurized source is achieved using timed valves with which the timing can be manipulated to control the volume of discharge to be released from the controller to the chamber. Contact of the discharge with the container containing a biological specimen initiates ice seeding inside the container at specified temperatures. The longer a valve is open, the larger the volume of the discharge. A separate valve serves each spray rail apparatus, thereby allowing the apparatus to be standardized for situations involving a plurality of spray rails and associated racks.

The ports comprise at least one inlet and at least one outlet for the pressurized liquefied or chilled gas source. A pressurized source is attached to an inlet port associated with the controller. Continuous from the port, the gas is ducted to the valves, which regulate the amount of gas discharged to the spray rails.

The rack selector allows the selection of which valves and associated spray rails will serve the rack or racks containing product to be seeded with ice. The timer regulates the amount of time the valves are open, thus the volume of discharge through the spray rails to the appropriate racks to be seeded.

The spray rail is a manifold that at one end receives liquefied or chilled gas from the valves via tubing or other ducting means. The spray rail comprises of a plurality of orifices to deliver an amount of liquefied or chilled gas at each level of a rack. These orifices are located in series along the manifold and each orifice contains a nozzle therein. The nozzles may also contain filter screens to prevent plugging. At the base of the spray rail there is a mounting foot to position and stably secure the spray rail to a baseplate or chamber floor.

The racks provide support during cryopreservation for the items to be cryopreserved as well as a means for transporting and storing the items in cold storage. The racks consist of parallel top and bottom plates supported by rails rigidly fixed perpendicularly to the plates therebetween. From the top plate of the rack are upwardly extending pins or pegs. In one mode of the invention, there are at least four pins equally distributed about the periphery of the plate. One pair of opposite pins are connected with a rod to form a handle. In the bottom plate are holes or recessions arranged in the same orientation as the pins on the top plate. The holes or recessions will align with the pins for stacking a rack atop another rack during cryopreservation or storage or to the pins upwardly extending from the baseplate along the floor of the chamber to align the rack proximal to the sprayrail.

In another mode of the invention, a handle is formed in the top plate by machining two oblong orifices on either side of the midline, or diameter, of the top plate. The top plate can be either grasped by hand or hooked to lift or maneuver the rack The rails of the rack are machined to have gaps to form horizontal planar surfaces equally distributed along the length of the rail, at about the same distances as the orifices of a sprayrail. The gaps are large enough to accommodate the bulk of an item, such as a petri dish or specialized container, to be cryopreserved. The rails, fixed perpendicularly between the top and bottom plates, are in parallel to each other. The rails are arranged so that the gaps are facing inwardly to the center of the rack, at about 90° angles, so two are facing opposite each other and the third in between. In this arrangement the gaps of the rails provide three points on which an item can be placed and supported. To maintain the items in position, a retention bar or rod is placed in the space 90° from the opposing rails, across from the central rail. In one embodiment, the bar is led down through a hole in the top plate to the bottom plate and is fastened in place to the bottom plate.

In a preferred embodiment, located between the two adjacent rails between each gap, there is an arc shaped plate, or driptray, oriented in parallel to the top and bottom plates. The driptrays are rigidly fastened between each gap to contain an item. The driptrays serve as a shield to prevent excess liquefied gas, such as freon, from dripping from an item to another item below, or overspraying from the nozzle onto the top of an item below the item being sprayed, which would subsequently result in unwanted ice seeding.

When the rack is positioned in the chamber according to the alignment pins, the gaps to contain items for cryopreservation will about evenly line up with the nozzles of the sprayrail. In turn, the drip trays will be aligned proximal to the sprayrail. The combination of the rack with the baseplate locating pins and sprayrails provides a reproducible distance between the spray nozzles and the sides of the items to be cryopreserved. Although this distance is consistent, the spray seeding method is tolerant of variations. The baseplate is a planar surface that is positioned along the bottom of the freezing chamber. The baseplate comprises of an organized pattern of pins and holes that allow one to locate the proper positions for the parts such as the spray rail, rack, etc. into the appropriate places on the baseplate.

FIG. 1 is a electronic schematic of the controller and includes a grounded power entry module 51; a fuse 52; a main power switch 53; a time delay-relay 54; a start button 55; an output indicator lamp 56; a single pole, multi position rotary switch 57; connecting terminals 58; and normally closed solenoid valves 59.

Power for the controller is provided by a grounded alternating current (AC) power source. Power entry module 51 is connected to the AC power source. Electrical overload is protected by fuse 52 connected in series adjacent to the power entry module 51. Main power switch 53, which controls the electrical flow to the controller, is serially connected to a digital time setting and readout time-delay relay 54 that controls the duration of the controller activation. Momentary push-button start switch 55 is serially associated with the time-delay relay 54 to initiate the action of the controller. Indicator lamp 56 is connected in parallel with the output of the relay 54 to indicate that the controller is activated. The time-delay relay 54 is serially connected to a single pole, multiposition switch 57 which is, in turn, serially connected to a plurality of normally closed solenoid valves 59. The series is completed by a parallel connection of the solenoid valves 59 back to the time-delay relay 54 and ultimately to the power entry module.

The amount of freon delivered by the ice seeding system is a function of the time the delivery valves are open. This duration of time the valves are open dictates the amount of freon discharged to the spray rails. This time is set on the time-delay relay on the front panel of the ice seeding controller. Before beginning a cryopreservation procedure, the tubing lines of the system should be purged of air by discharging liquefied gas from the spray rails for a sufficient interval of time.

Modifications and enhancements may be made to the controller by the skilled artisan by substituting one or more components of the electrical system and still achieve essentially the same controller functions of regulating liquefied gas flow to the sprayrails.

Figure 2A:
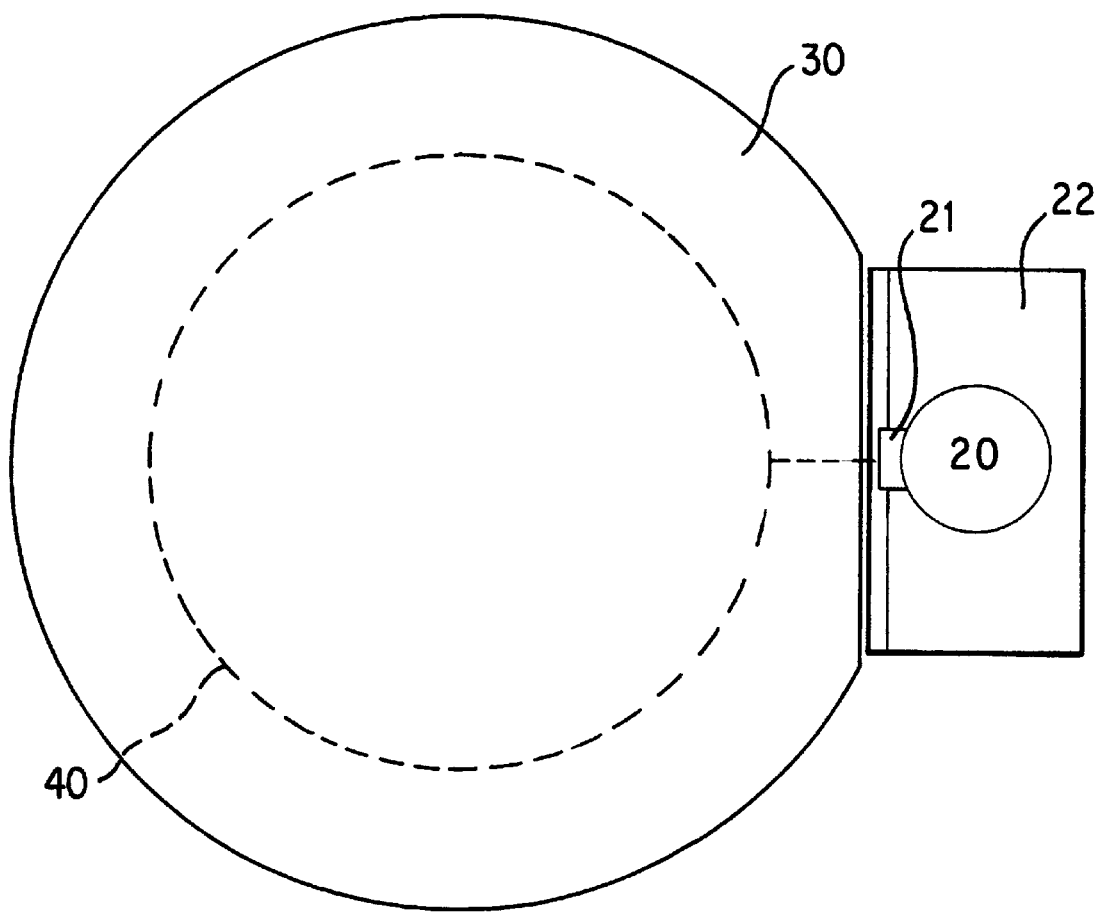
FIGS. 2A and 2B show views of a sprayrail proximal to a rack.
Figure 2B:
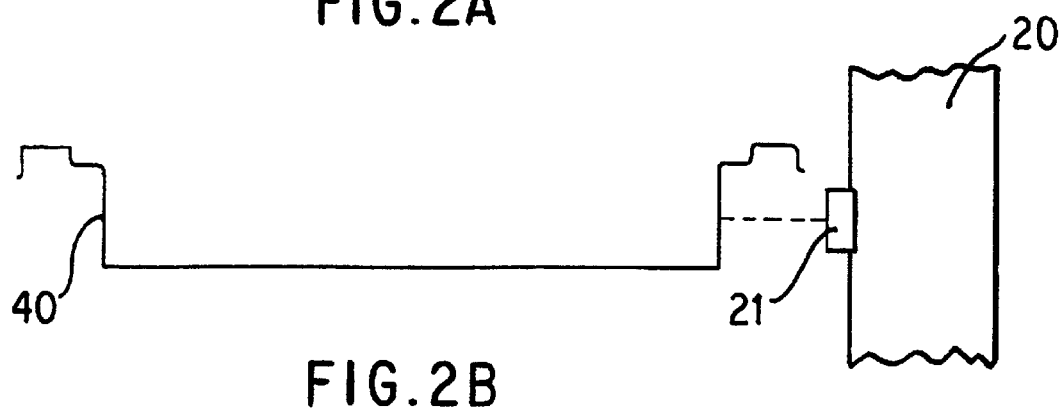

FIGS. 2A and 2B depict the association of the sprayrail with the rack. The top view of FIG. 2A shows a nozzle 21; sprayrail 20; mounting foot 22; rack 30; container 40. Side view of FIG. 2B shows a nozzle 21, a segment of sprayrail 20, and container 40. Nozzle 21 is mounted within an orifice of sprayrail 20. Sprayrail 20 is attached to a mounting foot 22 which is turn stably secured to a baseplate. Rack 30 is placed on the baseplate proximal to sprayrail 20, adjacent with mounting foot 22. The side of container 40 is centrally aligned with nozzle 21 to ensure that discharge from the nozzle is directed at the side of the container.

Figure 3A:
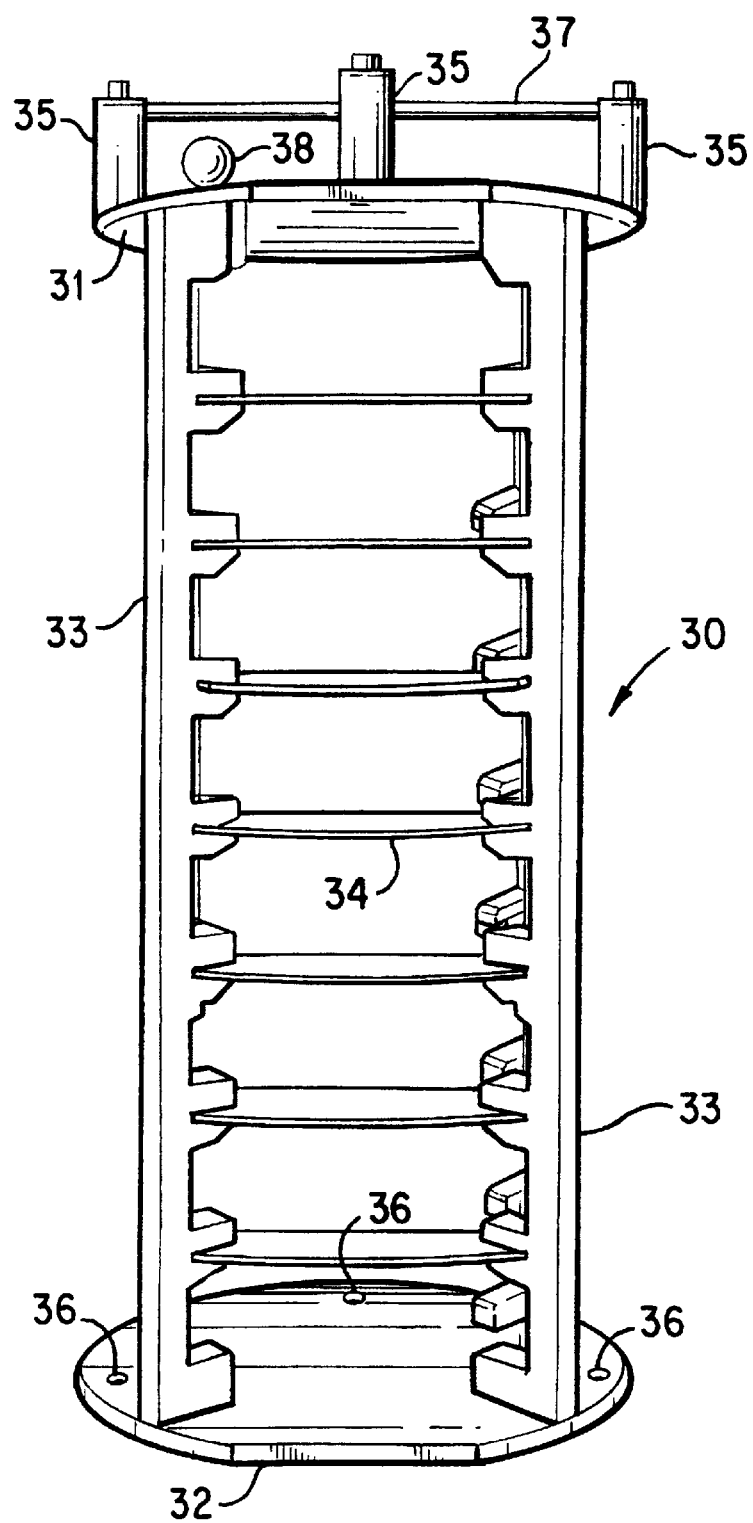
FIGS. 3A, 3B, and 3C show views and features of a rack.
Figure 3B:
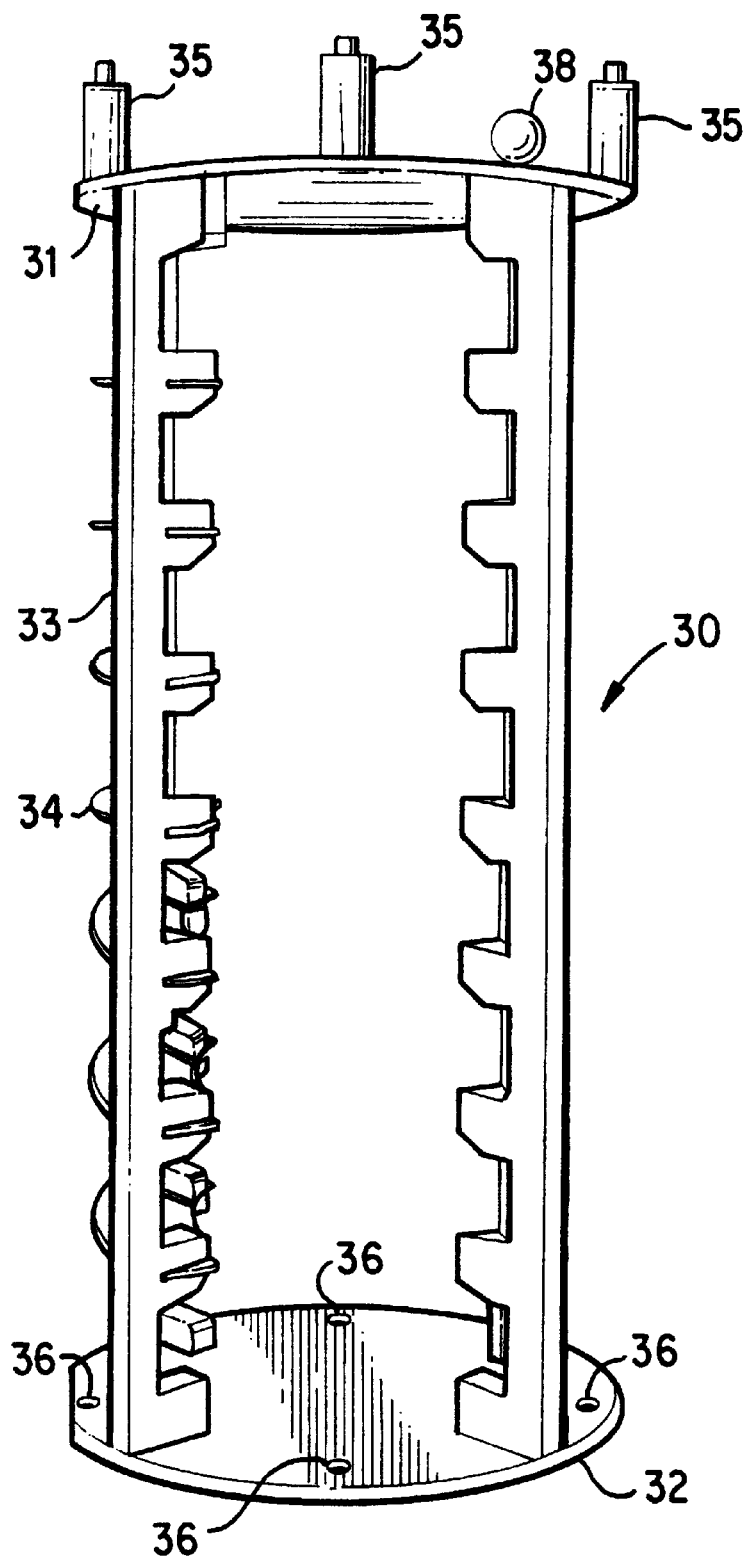
Figure 3C:
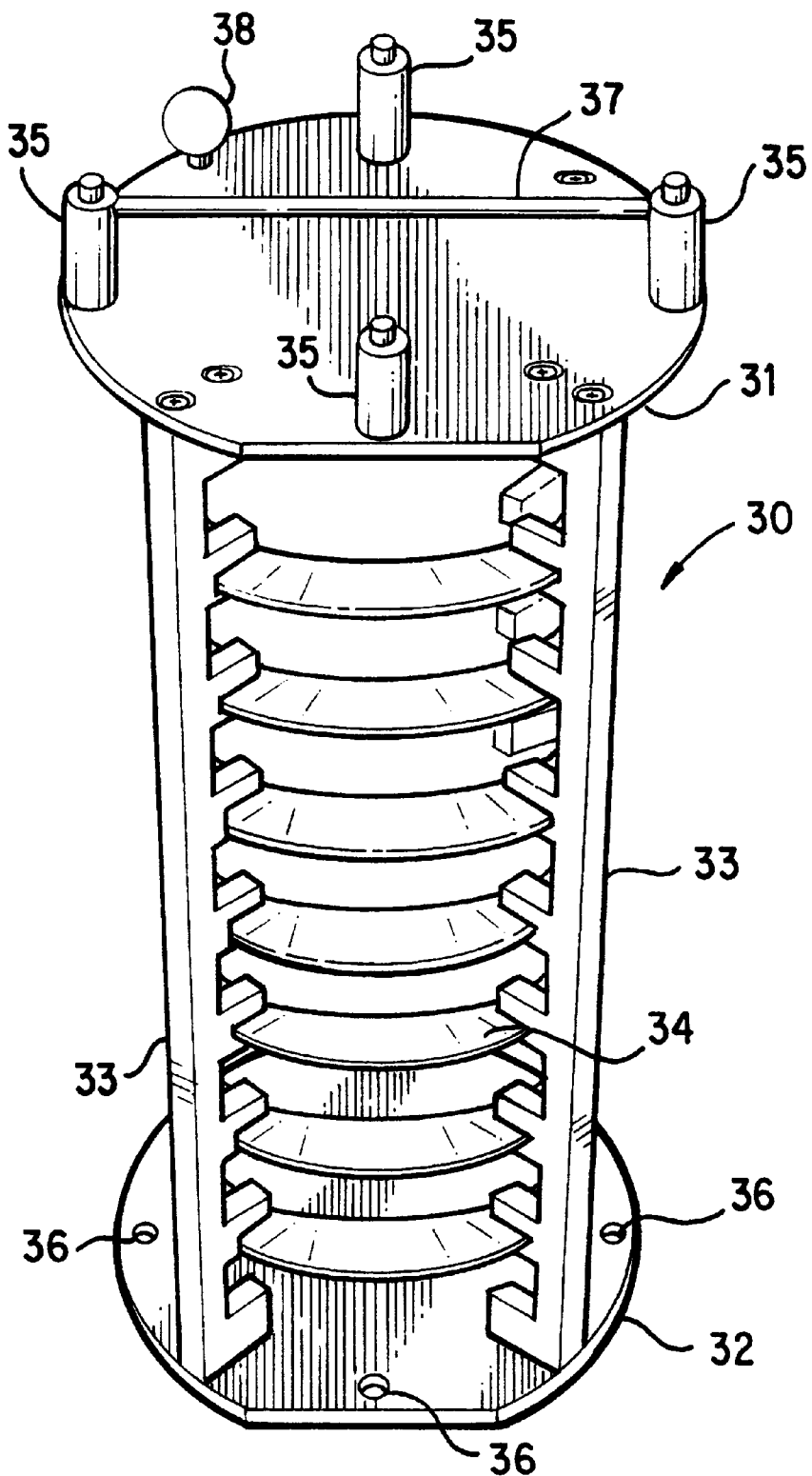

FIGS. 3A, 3B, and 3C show views of rack 30. Shown are rack 30; top plate 31; bottom plate 32; rails 33; driptray 34; locating pins 35; locating holes 36; handle 37; and handle for retention bar 38. The frame of rack 30 consists essentially of three rails 33 securely mounted to top plate 31 and bottom plate 32 at either ends of the rails. Rails 33 contain gaps equally spaced along the rails for placement of containers. In one mode of the invention, driptrays 34 are mounted between adjacent rails 33 along the side of rack 30 to be placed adjacent to the spray rail. Top plate 31 has upwardly extending locating pins 35 positioned along the periphery of the top plate with two opposing pins connected by a handle 37 therebetween. Bottom plate 32 has holes positioned along the periphery of the plate for mating with the locating pins 35 of top plate 31 or with those on the baseplate. A retention bar closes the large gap through which containers are placed in rack 30 by inserting the bar through a hole in top plate 31 down to a mount located on bottom plate 32 to prevent containers from falling out of the rack during positioning or storage.

Figure 4:
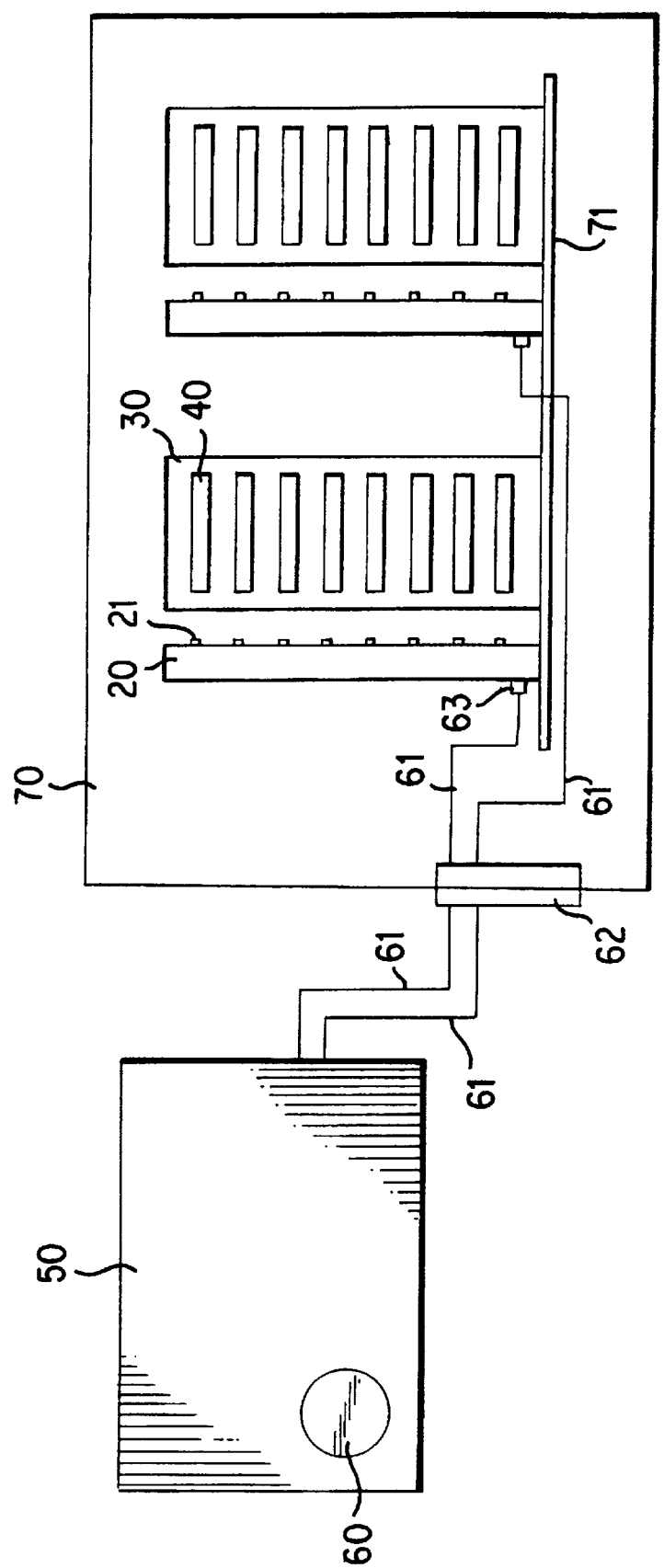
FIG. 4 shows a schematic of the ice seeding system and freezing chamber according to one embodiment of the present invention.

FIG. 4 is a schematic of the ice seeding system and freezing chamber. Shown are controller 50; inlet port for pressurized liquefied or chilled gas 60; lines 61; feedthrough plug 62; sprayrail inlet 63; sprayrail 20; nozzle 21; rack 30; container 40; chamber 70; and baseplate 71. Controller 50 contains an inlet port for pressurized liquefied or chilled gas 60. Discharge of the gas is mediated by the solenoid valves of the controller 50 and is delivered to the sprayrails 20 via lines 61. Feedthrough plug 62 allows passage of lines 61 into chamber 70 while maintaining the seal of the chamber. Lines 61 are connected to the sprayrails 21, containing a plurality of nozzles 21 at sprayrail 63 located at the mounting foot of the sprayrail. Liquefied or chilled gas is discharged from nozzles 21 to containers 40 held proximal in racks 30. Sprayrails 20 and racks 30 are stably secured to baseplate 71 within chamber 70.

Figure 5:
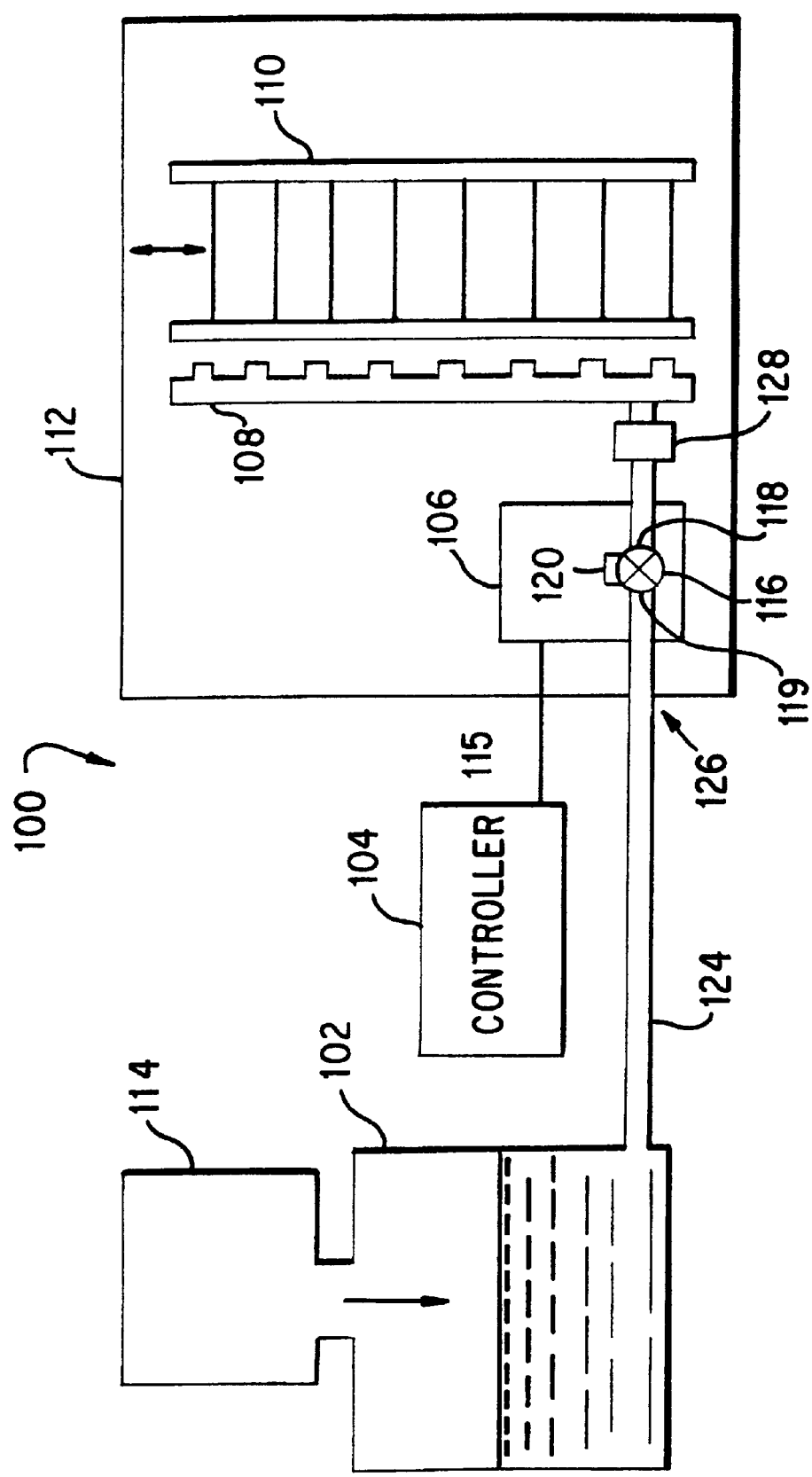
FIG. 5 is a part pictorial, part schematic view of an ice seeding system and freezing chamber according to another embodiment of the present invention.

Referring to FIG. 5, in another embodiment, a system 100 has a liquid supply 102, a controller 104, a valving manifold 106, and a sprayrail 108 with nozzles for directing the liquefied gas from supply 102 to containers on a rack 110 in a freezing chamber 112. Liquid supply 102 is pressurized from the top of supply 102 with a source 114 of gas pressure, preferably regulated nitrogen gas at 150 psig. While supply 102 can be kept continually under pressure, the container need only be pressurized once for multiple uses, because only small quantities of liquid are typically drawn from supply 102. If more fluid were drawn from the supply, the supply could be pressurized more frequently.

Valving manifold 106 is provided inside of freezing chamber 112 and preferably has eight valves 116 (only one of which is shown here) for directing the liquefied gas to one of eight sprayrails in response to control signals over electric signal line 115 from controller 104. Each valve is preferably a three-way valve having an inlet 119 for receiving the liquefied gas through line 124, one outlet 118 for providing liquefied gas to sprayrail 108, and a second outlet 120 vented to the atmosphere inside chamber 112. With a three-way valve, venting after the system is shut off depressurizes the spray rails without requiring several seconds of residual gas and liquid to be sprayed to the containers; rather, it takes less than a second, and the gas and liquid are immediately shut off from the containers when desired. By locating valving manifold 106 inside chamber 112, there is only one liquid line 124 extending through a feedthrough 126 from outside to inside chamber 112; moreover, there is better control over the liquid because there is less distance between the valves 116 and their respective sprayrails 108. A filter 128 is provided between valve 116 and sprayrail 108 to trap particles that can cause clogging at the nozzles.

While only one sprayrail is shown for use with one rack having eight levels for holding containers, the device of the present invention can be used with multiple sprayrails, in which case there are multiple valves, filters, and sprayrails. In another alternative, a sprayrail can be provided with 16 nozzles at 16 different vertical levels, in which case, two racks can be stacked one on top of the other, and appropriately located relative to each other with positioning pins.

As an alternative to the nitrogen pressure on the liquefied gas supply, a gear pump can be used to provide fluid at a pressure well above the phase transition.

An alternate setup for large volume freezing to enable larger lots of living tissue or equivalents to be cryopreserved at one time consists of a large chamber outfitted with a large area baseplate with a greater number of positions for the location of spray rails and racks. Additional components can be incorporated to the existing controller arrangement Sprayrails can be extended to a longer length to continue the manifold to another series of orifices. Racks can be stacked as the bottom plates of the racks contain holes to accommodate pins of the top plate of the rack below. The controller may also be integrated within the freezing chamber itself and further modified with sensors and controls to initiate the ice seeding when the chamber temperature reaches a specific point. Other mechanisms can be added to provide chamber air circulation.

A preferred element or compound of liquefied or chilled gas for use in the cryopreservation system is one that undergoes a phase change from liquid to gas at a temperature below the freezing temperature of the cryopreservation solution in the package. The liquefied or chilled gas used must be under pressure. Pressure can be provided by using the natural expanding qualities of the liquid or gas; by providing a propellant mixed with the liquefied or chilled gas; or by mechanical means by employment of a pump. When a small amount of the gas is delivered by way of the apparatus to the side of the package, the phase change of the liquefied gas to a vapor, i.e., evaporation, causes cooling of the package wall at the point of contact to temperatures below the freezing temperature of the cryopreservative, sufficiently low to form a seed of ice in the cryoprotectant within the package.

The freezing temperature of the cryopreservation medium varies as it is dependent on the nature of the components contained in the medium. Most cryopreservatives are water based but also contain salts and glass forming agents that affect the freezing temperature of the cryopreservative. Glass forming agents prevent the crystallization of the cryopreservative to protect the cells or tissue to be frozen from cryofracture (cracking of the frozen tissue due to crystal formation), thus maintaining viability of the cells or tissue. A cryoprotectant medium may contain "cell penetrating glass forming agents" or "non-cell penetrating glass forming agents" or both. The cell penetrating glass forming agent is preferably glycerol, but may include propylene glycol, ethylene glycol, dimethylsulfoxide, and other penetrating glass forming agents known in the art. Non-cell penetrating glass forming agents include high molecular weight forms of complex carbohydrates, such as chondroitin sulfate, polyvinylpyrrolidone, polyethylene glycol or hetastarch, such as hydroxyethyl starch. The cell penetrating glass forming agents and/or non-cell penetrating glass forming agents are diluted in a base of a physiological pH. The base is preferably DMEM, but may be substituted with phosphate buffered saline, IDMEM, MEM, M199, RPMI 1640, Ham's F-12 Ham's F-10, NCTC 109, NCTC 135, or combinations thereof. The preferred cryoprotectant solution contains 1.5M to 2.5M glycerol, preferably 2M glycerol, in a base of Dulbecco's Modified Eagle's Medium (DMEM). These solutions can be modified and optimized by one of skill in the art using known cryoprotectants and freezing, storing, thawing, and rinsing procedures that are compatible with maintaining maximal viability, depending on the particular application. The selection of a gas source to be used in accordance with the invention should take into consideration the nature of the cryopreservative in which the ice seeding is to be initiated. Those skilled in the art will be able to determine a proper combination of gas and cryopreservative compatible with the material to be cryopreserved and the liquid-solid equilibrium temperature of the cryopreservative required to perform ice seeding.

A preferred gas source is freon compound HFC-134a (1,1,1,2 tetra-fluoroethane) which contains no ozone-depleting chlorine, thus it is not targeted for phase-out by the Environmental Protection Agency (EPA). The temperature at which the freon compound HFC-134a evaporates is nominally between −25 to −30° C., sufficiently low to guarantee formation of ice. Other liquefied gasses that evaporate at a sufficiently low temperature to induce ice formation would include liquid nitrogen ($LN_2$), isopentane, propane, and other fluorocarbons such as Freon 12 and Freon 22; however, some of these gasses have their drawbacks.

As it is well known, isopentane (also known as 2-methyl butane) is a neurological, respiratory, and hepatic toxin to humans. Since it is toxic to humans, it presents a danger of adverse health effects to any nearby persons who inhale them, especially those persons performing the freezing of the specimen. Also, isopentane is flammable and poses a danger of fire or explosion. Isopentane is denser than air and can easily move some distance from the apparatus in which the freezing procedure is being performed. Thus, if the isopentane reaches a source of ignition, it will ignite or explode. Additionally, fluorocarbons pose a threat as well. Freon 12, Freon 22 and dichlorofluoromethane are chlorofluorocarbons (hereafter, abbreviated as CFCs). If a CFC is employed as the fluid for freezing, a hazard arises in that CFCs are detrimental to the protective ozone layer of the earth. As a result, the United States Government has imposed regulations requiring the phase-out of several CFCs for all but certain uses that are critical to the preservation of human life. Hence, it is desirable to find a hazard-free method of cryopreserving specimens with a liquefied gas that not only will be suitable at extremely low temperatures, but also will be non-toxic to humans, non-flammable and environmentally safe.

Rather than a liquefied gas, a chilled gas under pressure may alternately be discharged from the spray rails. The temperature of the chilled gas would be required to be well below the solid-liquid equilibrium temperature of the cryoprotectant in the container. The gas may be nitrogen, oxygen, carbon dioxide or simply air. Any gas may be used provided that it be under pressure and appropriately chilled. Chilling may be obtained through expansion of the pressurized gas.

In the preferred embodiment, the cryopreservative is Dulbecco's Modified Eagle's Medium (DMEM), a common cell culture media base, containing glycerol, a cell penetrating glass forming agent, at a 2M concentration. The equilibrium freezing point of DMEM/2M glycerol is about −5.2° C. Ice seeding must then be accomplished at −6° C. +/−0.5° C., a temperature range slightly below the equilibrium freezing point, −5.2° C., of the cryoprotectant solution used. Seeding must occur below −5.2° C., since ice formed above this temperature may melt before cooling proceeds below this point.

Control of the temperature at which the solid phase (ice) begins to form, as well as the cooling rate after its formation, is required to control the degree of dehydration of the tissue. The equilibrium phase diagram for glycerol-water solutions relates to both the amount of ice and the amount of remaining solution over temperature. Since ice, as it forms, rejects solutes, the solution in equilibrium with the ice becomes more concentrated as the temperature is lowered. This increasing solute concentration in the extracellular solution provides an osmotic gradient which causes water to be removed from the cells. If sufficient water is not removed at relatively high sub-zero temperatures, ice can precipitate within the cells, an event associated with cell and/or tissue damage. If seeding of the extracellular fluid is not performed deliberately, ice will appear spontaneously at temperatures ranging from the equilibrium point for the starting solution, −5.2° C., to as low as −40° C. The lowest temperature at which spontaneous seeding has been observed in the packages is −14° C. The lower the temperature of the spontaneous event, the greater the likelihood that significant amounts of water will be trapped and frozen within the cells or tissue, thus the greater the degree of damage. Since the spontaneous seeding can occur over a wide temperature range and can vary from package to package, survival rates of cells between similar tissues can vary widely. For the above described situation, the seeding operation should achieve a localized region of cooling with the temperature of the localized cooling below −15° C. to guarantee formation of the seed.

The amount of ice that must be produced by the seeding operation is not critical to the success of the cryopreservation process as long as some ice is formed. At −6.0° C., the amount of ice that must be present in equilibrium with the remaining solution is about 0.36 g, for a starting solution of 16 mL of 2.0 M glycerol in DMEM. This quantity of ice should be the total present above and below the plane of the tissue. It is acceptable for the seeding operation to produce less or more than this amount, provided sufficient time is allowed for equilibrium to be established by the growth or melting of ice. It is best to control the process to produce excess ice, provided the region in which the ice is formed does not encompass the area of the tissue and is allowed to achieve equilibrium with the solution in the package. A rough estimate of the amount of HFC-134a required to produce this amount of ice can be obtained from the HFC-134a properties. Since the material absorbs approximately 217 joules/g in going from liquid to gas at 1 atmosphere, and the latent heat of fusion for water is 333 joules/g, about 0.56 g of Freon are required to produce about 0.36 g of ice. The volume of liquefied gas to be discharged can be determined and optimized by one of skill in the art to form an ice seed within an amount of cryoprotectant.

The following examples are provided to better elucidate the practice of the present invention and should not be interpreted in any way to limit the scope of the present invention. Those skilled in the art will recognize that various modifications can be made to the methods described herein while not departing from the spirit and scope of the present invention.

EXAMPLES

Example 1

Cryopreservation of Living Skin Equivalents (LSE) Using the Ice Seeding System

Living Skin Equivalent (LSE) constructs were prepared in accordance to U.S. Pat. No. 5,536,656, which is expressly incorporated herein by reference. LSEs and attached 75 mm carrier inserts (TRANSWELL®, Costar, Cambridge), at 7 to 12 days post air lift, were placed in 100 mm petri dishes (Costar). LSE constructs were perfused with cryoprotectant by submerging the constructs and the transwell with 25 mL of cryoprotective media, 2M Glycerol in DMEM, in the 100 mm petri dish for one hour. During perfusion, the constructs were agitated for one hour on an orbital shaker (Bellco) at 70 rpm in a 10% $CO_2$ gassed chamber. Agitation allows for more complete perfusion and better reproducibility of the cryopreservation method. After LSE were perfused, the petri dishes containing LSE, carrier inserts and extracellular freezing media (2M Glycerol and DMEM) were placed in a cryopreservation package and heat sealed. Cryopreservation packages are described in patent publication, no. WO 96/24018, which is expressly incorporated herein by reference.

The chamber of a programmable freezer (Planar) was outfitted with the invention described herein. The freezer was set at a starting temperature of 20.0° C. The tubing lines were purged with freon for a single one second interval to remove any air in the lines. Packaged LSE units were placed securely into racks accommodating eight LSE units each. The racks, guided by locating pins, were placed adjacent to the spray rails. The chamber door of the freezer was closed to seal the chamber from the external environment.

LSE units were cooled at −10° C/minute to −6° C. and the chamber temperature was held at −6° C. for 40 minutes to equilibrate the cryoprotectant and perfused constructs to the chamber temperature. After the 40 minute hold, extracellular ice was initiated by directly discharging freon for one second at dose proximity to the side of the package. The freon, as it evaporated from the surface of the package, caused the contact area of the freon to drop in temperature enough to initiate extracellular ice formation.

After all LSE units were seeded with ice crystals, the units are allowed to equilibrate for one hour at −6° C. The chamber temperature was then cooled at −0.07° C./minute to a final temperature of −20° C. The chamber was then cooled at −0.5° C/min to a final temperature of −70° C. Once the LSE units were cryopreserved, they were transferred to a vapor phase storage tank (Dewar) at a temperature of −120° to −150° C.

Although the foregoing invention has been described in some detail by way of illustration and example for purposes of clarity of understanding, it will be obvious to one skilled in the art that certain changes and modifications may be practiced within the scope of the appended claims.

What we claim is:

1. Ice seeding apparatus for the cryopreservation of biological samples with a chilled fluid suitable for cryopreservation, the apparatus comprising:
   a cryopreservation freezing chamber;
   a rack in the chamber for holding a number of containers for holding biological samples;
   a sprayrail in the chamber and having nozzles for directing the chilled fluid to the containers on the rack;
   a three-way valve in the chamber, controlled by the controller, and having an inlet for receiving the chilled fluid, a first outlet for providing the chilled fluid to the sprayrail, and a second outlet for venting the chilled fluid into the chamber,
   a controller controlling the valve and the flow of chilled fluid.

2. The apparatus of claim 1, wherein the rack is vertically oriented to hold containers at different vertical levels, and the sprayrail has nozzles oriented at the same vertical levels as the containers and positioned to be close to the containers.

3. The apparatus of claim 1, wherein the rack is removable from the chamber, and wherein the nozzles of the sprayrail are positioned to be close to the containers when the rack holding the containers is provided in the chamber.

4. The apparatus of claim 1, wherein the rack has parallel top and bottom plates supported by rails extending perpendicular to and connected to the top and bottom plates.

5. The apparatus of claim 4, wherein the top plate has a plurality of openings sized and configured to form a handle that can be grasped by hand.

6. The apparatus of claim 1, wherein the fluid is a gas.

7. The apparatus of claim 1, wherein the fluid is a liquid.

8. The apparatus of claim 1, further comprising containers and biological samples in the containers.

9. The apparatus of claim 1, wherein there are a plurality of sprayrails, racks, and valves, with each valve associated with a sprayrail and each sprayrail associated with a rack.

10. Ice seeding apparatus for the cryopreservation of biological samples with a chilled fluid suitable for cryopreservation from a source, the apparatus comprising:
    a cryopreservation freezing chamber;
    a plurality of racks, each for holding a number of containers for containing biological samples in the chamber;
    a plurality of sprayrails, each mounted in the chamber and having nozzles for directing an amount of the chilled fluid to the containers on a rack associated with that sprayrail; and
    a valving manifold located in the chamber and having a plurality of valves, with a valve associated with each one of the sprayrails for providing chilled fluid to the sprayrail.

11. The apparatus of claim 10, further comprising a controller for regulating the amount of chilled fluid directed from the source of chilled fluid to the containers.

12. The apparatus of claim 10, wherein the rack is vertically oriented to hold containers at different vertical levels, and each sprayrail has nozzles oriented at the same vertical levels as the containers and positioned to be close to the containers.

13. The apparatus of claim 10, wherein the valves are three-way valves mounted in the chamber, each valve being associated with a sprayrail and having an inlet for receiving the chilled fluid, a first outlet for providing the chilled fluid to the associated sprayrail, and a second outlet for venting the chilled fluid into the chamber.

14. The apparatus of claim 10, wherein the rack is removable from the chamber, and wherein the nozzles of the sprayrail are positioned to be close to the containers when the rack holding the containers is provided in the chamber.

15. The apparatus of claim 10, wherein the chamber has a single feedthrough for providing fluid from outside the chamber to the valving manifold.

16. The apparatus of claim 15, wherein the valves in the valving manifold are three-way valves mounted in the chamber, each valve being associated with a sprayrail and having an inlet for receiving the fluid, a first outlet for providing the fluid to the associated sprayrail, and a second outlet for venting into the chamber.

17. The apparatus of claim 10, further comprising a filter between the valving manifold and the sprayrail.

* * * * *